United States Patent [19]
Walls et al.

[11] 4,169,465
[45] Oct. 2, 1979

[54] METHOD AND APPARATUS FOR OBTAINING NON-INVASIVE CARDIO-PULMONARY MEASUREMENTS

[75] Inventors: James A. Walls, 71 Hampton Park E., Branford, Conn. 06405; Robert P. Howard, E. Hartford, Conn.

[73] Assignee: James A. Walls, Branford, Conn.

[21] Appl. No.: 793,513

[22] Filed: May 4, 1977

[51] Int. Cl.² .............................................. A61B 5/08
[52] U.S. Cl. .................................. 128/719; 128/145.6
[58] Field of Search ................. 128/142.2, 142.3, 2 A, 128/2.07–2.08, 145.5–145.8

[56] References Cited

U.S. PATENT DOCUMENTS

| | | | |
|---|---|---|---|
| 2,766,753 | 10/1956 | Koch et al. | 128/145.8 |
| 3,046,979 | 7/1962 | Andreasen | 128/145.8 |
| 3,467,092 | 9/1969 | Bird et al. | 128/145.6 |
| 3,499,438 | 3/1970 | Manley | 128/145.6 |
| 3,527,205 | 9/1970 | Jones | 128/2.08 |
| 3,659,590 | 5/1972 | Jones et al. | 128/2.08 |
| 3,666,955 | 5/1972 | Supremont et al. | 128/2.08 |
| 3,759,249 | 9/1973 | Fletcher et al. | 128/2.08 |
| 3,769,966 | 11/1973 | Youdin et al. | 128/2 A |
| 3,881,463 | 5/1975 | LeMon | 128/2 A |
| 3,910,261 | 10/1975 | Ragsdale et al. | 128/2.07 |
| 3,957,033 | 5/1976 | Winchell et al. | 128/2 A |

FOREIGN PATENT DOCUMENTS

| | | | |
|---|---|---|---|
| 685702 | 8/1959 | Canada | 128/145.8 |
| 1031049 | 5/1966 | United Kingdom | 128/145.6 |

OTHER PUBLICATIONS

Coles, J. R. et al., "Computer Control of Respiration & Anaesthesia", Med. & Biol. Engr., May 1973, pp. 262–267.

*Primary Examiner*—Robert W. Michell
*Assistant Examiner*—Francis J. Jaworski
*Attorney, Agent, or Firm*—DeLio and Montgomery

[57] ABSTRACT

A method and apparatus for obtaining non-invasive cardio-pulmonary measurements, without voluntary patient cooperation, by means of an inhalation indicator dilution rebreathing device having a valving system and test gas chamber connected to a volume ventilator, the valving system being operable to connect the ventilator directly to the patient for normal ventilation or to effect inhalation and exhalation of the test gas during the measurement cycle, the test gas being monitored and analyzed by a test instrument such as a mass spectrometer to ascertain the cardio-pulmonary parameters.

8 Claims, 4 Drawing Figures

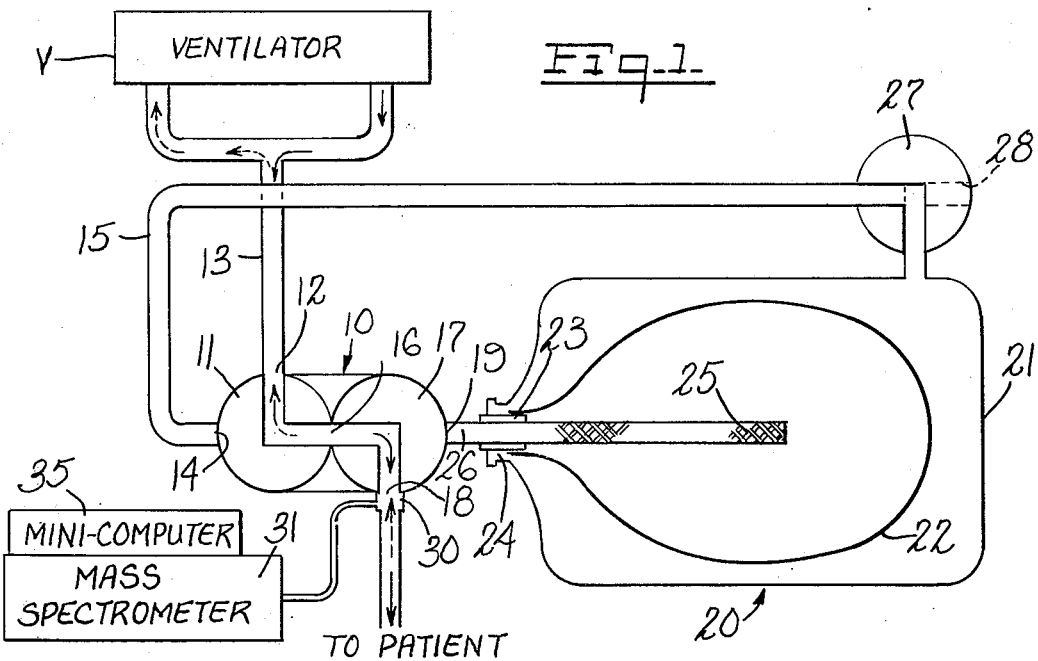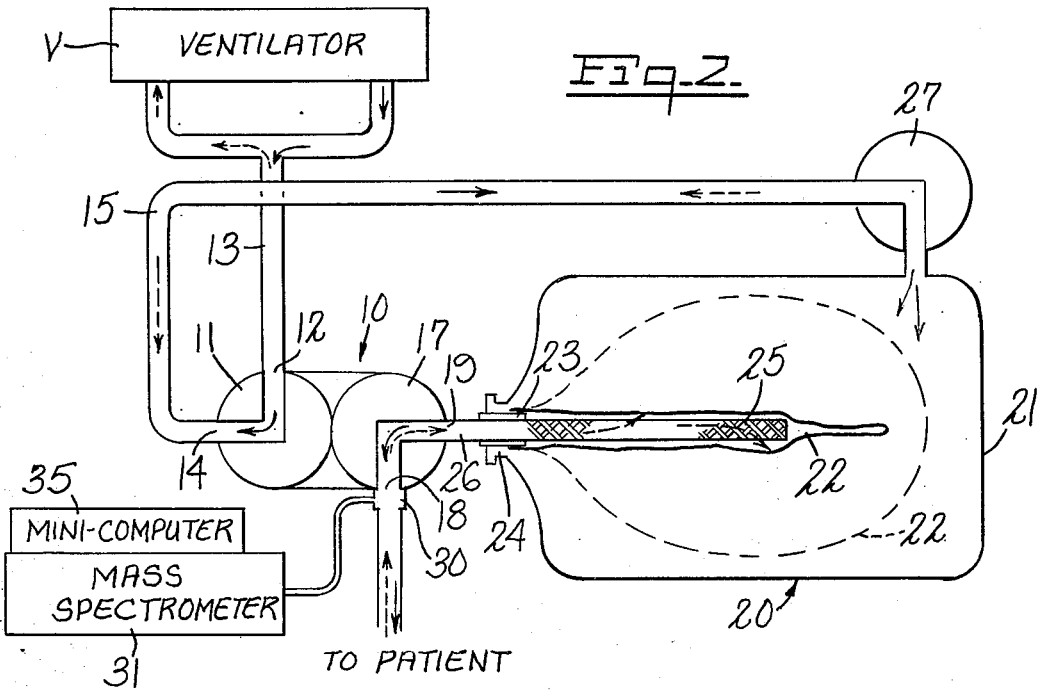

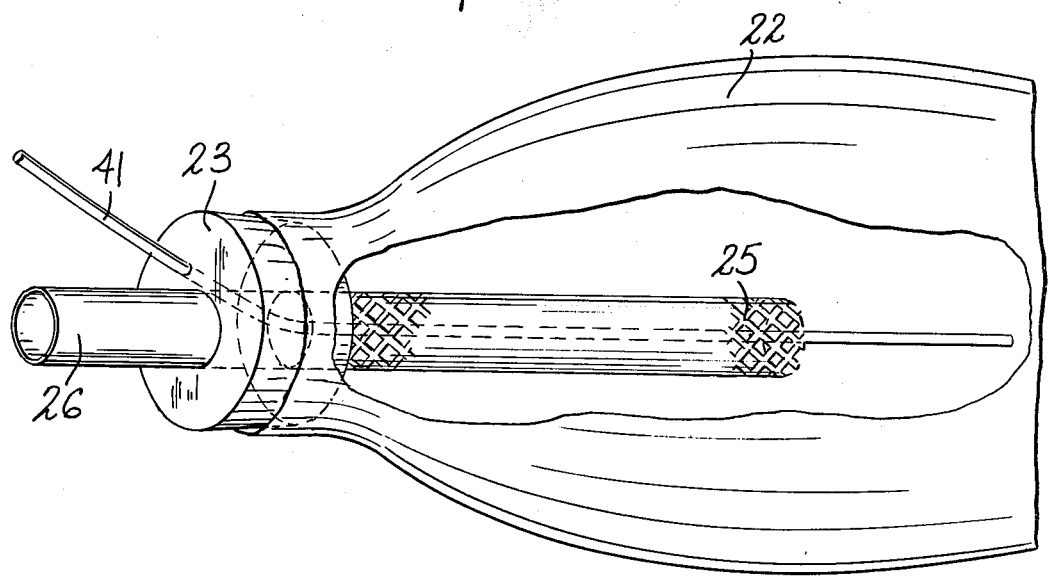
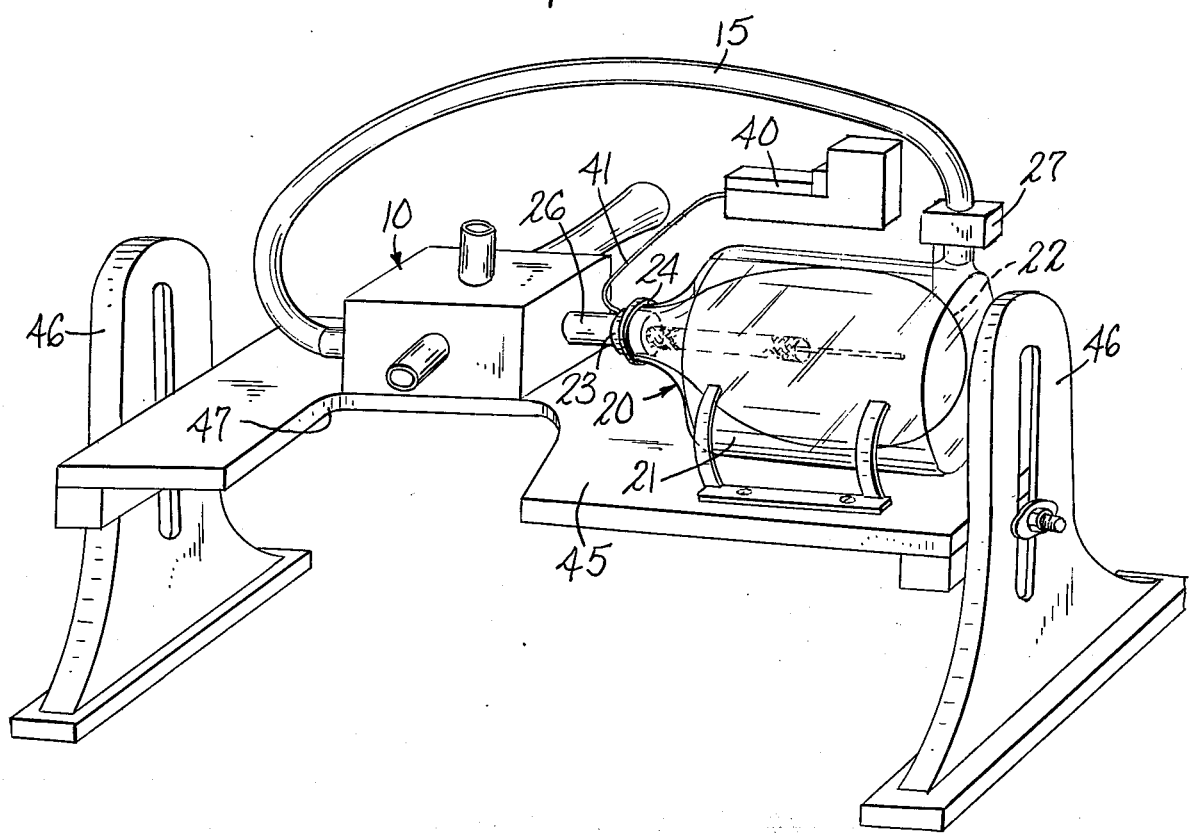

METHOD AND APPARATUS FOR OBTAINING NON-INVASIVE CARDIO-PULMONARY MEASUREMENTS

This invention relates to a method and apparatus for obtaining non-invasive cardio-pulmonary measurements, without voluntary patient cooperation, by means of an inhalation indicator dilution rebreathing device having a valving system and test gas chamber connected to a volume ventilator, the valving system being operable to connect the ventilator directly to the patient for normal ventilation or to effect inhalation and exhalation of the test gas during the measurement cycle, the test gas being monitored and analyzed by a test instrument such as a mass spectrometer to ascertain the cardio-pulmonary parameters.

The rebreathing technique was developed by Sackner et al (1) and Begin et al (2), to assess pulmonary and hemodynamic parameters in adults, without subjecting them to undesirable hazards. This procedure allows non-invasive determination of lung diffusing capacity ($D_{LCO}$), effective pulmonary blood flow ($QEP$), lung tissue volume ($V_T$), and functional residual capacity ($V_{FRC}$). Prior procedures have, however, required patient cooperation in performing the rebreathing maneuver.

(1)Sackner, Marvin A.; Greeneltch, Delmos; Helman, Martin S.; Epstein, Sanford; Atkins, Neil; Diffusing Capacity, Membrane Diffusing Capacity, Capillary Blood Volume, Pulmonary Tissue Volume, and Cardiac Output Measured by a Rebreathing Technique. Am. Rev. of Resp. Disease. 3, pp. 157–165. 1975.
(2)Begin, Raymond; DeGraff, Arthur, Jr.; Gardner, Reed M.; Hall, Lawrence G.; Howard, Robert P.; Johnson, Robert Wolsen, Robert; Sackner, Marvin A.; Test of a Rebreathing Technique for Measuring Cardiac Output, Diffusing Capacity and Pulmonary Tissue Volume. XV Meeting of the Scandinavian Society for Clinical Chemistry and Clinical Physiology, AARUS, Denmark, June 25-27, 1975.

The identification of an infant at risk with heart or lung disease is often a problem confronting the neonatologist or pediatric cardiologist. The only present objective methods of assessing the status of a child in distress is by plain chest x-ray, electrocardiography, and blood gas determinations. Physical examination is a very subjective tool and is often misleading. The determination of either primary lung or heart disease may require hazardous cardiac catheterization. Use of a rebreathing technique may allow the differentiation between diseases without endangering the child and delaying appropriate therapy. The effects of therapy could also be assessed by this same method.

As heretofore known the rebreathing technique does not lend itself usefully to many critically ill patients who cannot voluntarily respond. This incapacitation usually means that other types of procedures, mostly invasive and potentially hazardous, must be performed.

The herein-disclosed invention provides a rebreathing apparatus which comprises a valving system and test gas chamber interfaced with a volume ventilator or a smaller pediatric ventilator, which serves as the gas propeller. The valving system, which may be in the form of two three-way valves, allows two modes of operation. In the first mode the subject is maintained on continuous ventilatory assistance. Initiation of the rebreathing procedure activates the second mode of operation. Here the ventilator rechannels its air flow to pressurize a bottle containing a sample of the test gas. The gas is forced into the subject's lungs during the ventilator's inhalation cycle. During exhalation, the bottle depressurizes and the subject's chest and lung compliance expels the gas back into the bag. This cyclic procedure continues for approximately fifteen seconds. The test is concluded by returning the subject to the original ventilatory assistance mode.

The gas mixture used for the rebreathing procedure may suitably consist of 5% helium, 0.5% carbon monoxide, 0.5% acetylene, and a balance of oxygen and nitrogen. A test instrument such as a mass spectrometer is employed to analyze the test gas and monitor the disappearance rates of these trace gases, plus oxygen and carbon dioxide concentrations as the subject rebreathes in a closed system. A mini-computer records these concentrations with respect to time.

By directly measuring and computing these hemodynamic and pulmonary parameters, it may become possible to determine the levels and effects of these factors in the newborn with critical heart and lung disease. There have been no prior direct measurements of these parameters in infants and as a result many of the assumptions made about the pathogenesis and intrinsic pathology of the lung, have been inferred only from secondarily derived data. Cardiac catheterization is often necessary to differentiate heart and lung disease and repeated studies are often needed to measure the effects of any therapy.

The same device can be enlarged to accommodate the critically ill adult. Alternate methods of achieving these parameters are traumatic, hazardous and almost always invasive. The sensitive condition of these patients makes a non-invasive procedure most advantageous.

It is an object of the invention to provide a new and improved method and apparatus for medical testing using an inhalation indicator dilution rebreathing technique which does not require patient cooperation.

It is another object of the invention to provide a method and apparatus which can be used with neonates, particularly to aid in early recognition of disease states and in assessment of the efficacy of therapeutic measures.

It is a further object of the invention to provide such a method and apparatus for ascertaining, without patient cooperation, the pulmonary and hemodynamic parameters pertinent to congenital heart and lung disease, particularly in neonates.

The invention accordingly comprises the several steps and the relation of one or more of such steps with respect to each of the others, and the apparatus embodying features of construction, combinations of elements, and arrangement of parts which are adapted to effect such steps, all as exemplified in the following detailed disclosure, and the scope of the invention will be indicated in the claims.

A practical embodiment of apparatus suitable for use in the method outlined above is shown in the accompanying drawings, wherein:

FIG. 1 represents diagrammatically the essential elements in their normal ventilation phase;

FIG. 2 represents the same elements in their test gas rebreathing phase;

FIG. 3 is a detail perspective view of the stopper with supplemental gas supply; and FIG. 4 is a somewhat diagrammatic perspective view of parts of the apparatus assembled on a suitable stand.

Referring to the drawings, the apparatus is shown as comprising a valve assembly 10, and a gas-bottle assembly 20, and a ventilator V.

The valve assembly is shown as a pair of three-way valves, for convenience of illustration, but the required functions could readily be combined in a single unit. The first valve portion 11 has a port 12 connected to the ventilator by a tube 13, a port 14 connected to the gas-bottle assembly by the tube 15 and a passage 16 into the second valve portion 17. The second valve portion has a port 18 connectable to the patient, and a port 19 connected to the gas-bottle assembly 20.

The gas-bottle assembly includes a rigid bottle 21 of constant volume and a gas bag or bladder 22 such as a cryovac polyethylene bag which should be impermeable to any of the gases used and can readily be inflated and deflated. The compliance of the bag is such that its inflation pressure is no greater than a few inches of water. Preferably the inflated bag fills most of the volume of the bottle. The neck of the gas bag is sealingly engaged with a stopper 23 fitting tightly in the neck 24 of the bottle and it is desirable to provide the stopper with a self-supporting fenestrated tube 25 projecting a substantial distance into the bag in order to support the bag in its collapsed state. The tube 25 is combined with or connected to a tube 26 which connects the port 19 with the interior of the bag 22. Adjacent the point where the tube 15 is connected to the bottle, a valve 27 is interposed for selectively venting the interior of the bottle to atmosphere through a port 28.

In the line from port 18 to the patient there is interposed a gas pick-up chamber 30 connected to a mass spectrometer 31, to sample and record changes in the composition of the test gases, signals from the spectrometer being instantly analyzed by a mini-computer 35.

During the course of a rebreathing test in neonatal applications, oxygen consumption by the neonatal patient and gas draw-off by the mass spectrometer for sampling can create a significant oxygen depletion which must be compensated for to avoid hypoxia. The amount of gas removed also tends to invalidate analytical equations based on volume constancy. For these reasons it is advisable to provide an infusion pump 40, supplying supplemental oxygen and nitrogen to the bag 22 through a capillary 41 passing through the stopper 23. The pump 40 is programmed to operate only when needed. The mixture is infused at a rate to maintain volume constancy, for which the analytical equations of the adult technique are based. The percentage of oxygen infused is sufficient to maintain a relatively constant alveolar concentration. The system equation can be expressed as:

$$V_{sys} = V_{syso} + (\dot{V}_{inf} - \dot{V}_{ms} - \dot{V}_{O2} + \dot{V}_{CO2})t \qquad (1)$$

where $V_{sys}$ = the system volume at any time; $V_{syso}$ = system volume at t=0; $\dot{V}_{O2}$ = rate of oxygen consumption; $\dot{V}_{CO2}$ = rate of carbon dioxide production; $\dot{V}_{inf}$ = rate of secondary infusion; $\dot{V}_{ms}$ = drawoff rate of mass spectrometer. Because of the large tidal volumes involved in adult testing, infusion is not required when testing adult patients.

The valve assembly 10 is adapted for adjustment to two modes of operation. According to FIG. 1 the valve portions are set up to present an open passage between the ventilator and the patient, through tube 13, port 12, passage 16, port 18, gas pick-up chamber 30 and a patient-attached device, not shown, such as an endotracheal tube, nasal cannula or low dead space face mask. With the flow circuit in this mode the patient can receive ventilatory support prior to and after testing.

To initiate the rebreathing maneuver, the valve assembly is adjusted to the positions of FIG. 2, wherein a passage is established through the tube 13, port 12, port 14, tube 15, valve 27 and bottle 21. The second valve portion 17 is adjusted to open a passage from the bag 22 through tubes 25 and 26 and port 19 to port 18, chamber 30 and on to the patient. When this circuit is operative the ventilator's air flow is directed to and from the bottle 21. The inhalation cycle pressurizes the chamber in the bottle, compressing the bag of test gas (shown full in broken lines) and propelling the gas into the patient's alveolar environment, at a rate equal to the rate of inhalation provided by the ventilator when adjusted as in FIG. 1. During the ventilator's exhalation cycle the chamber in the bottle is depressurized and the patient's lung and chest compliance expel the gas back into the rebreathing bag (shown empty in full lines), by way of the pick-up chamber 30 where a sample is analyzed by the spectrometer and the results printed out by the mini-computer. This cyclic procedure is continued throughout the test period, normally for 15 seconds, after which the valve elements are returned to the FIG. 1 position and normal ventilation continued as needed.

The gas mixture used for the inhalation indicator dilution rebreathing procedure may consist of 5% helium, 0.5% carbon monoxide, 0.5% acetylene and the balance of oxygen and nitrogen, the latter preferably being supplied in a preselected ratio duplicating the pretest ventilatory oxygen concentration. When infusion is required to correct for depletion of oxygen during a test and to maintain volume constancy, the infused gas preferably has a higher ratio of oxygen to nitrogen, so as to maintain the test gas at the preselected ratio. The test gas is introduced into the bag 22 initially by deflating the bag with the port 28 open, to vent the interior of the bottle, and then supplying a known quantity of the gas mixture to the bag through the vents 18 and 19, then closing port 28 before connecting the apparatus to the patient, or otherwise.

FIG. 4 shows the valve assembly 10 and gas-bottle assembly 20 mounted on a stand which includes a platform 45 adjustably supported by end posts 46, spaced far enough apart to permit the table to span the chest portion of a supine patient. The table is shown as having a cut-out recess 47 to permit the apparatus to be connected to the patient's intubation with a minimum of additional tubing.

While the gas-bottle assembly is shown as a simple and convenient device for the intended purpose, it would be possible to substitute a loose diaphragm or slidable piston as the means for isolating the test gas from the air in the constant volume chamber (bottle).

It will thus be seen that the objects set forth above, among those made apparent from the preceding description, are efficiently attained and, since certain changes may be made in carrying out the above method and in the constructions set forth without departing from the spirit and scope of the invention, it is intended that all matter contained in the above description and shown in the accompanying drawings shall be interpreted as illustrative and not in a limiting sense.

What we claim is:

1. A method for obtaining non-invasive cardio-pulmonary measurements which includes, providing a volume ventilator, a valving system, an indicator dilution gas container and means for sampling and testing for variations in characteristics of the indicator dilution gas, using the ventilator to directly assist ventilate the patient, actuating the valving system to connect the ventilator to the indicator dilution gas container, causing the pneumatic action of the ventilator to move the indicator dilution gas into the patient's lungs in a rebreathing maneuver, sampling the indicator dilution gas and recording variations in the characteristics of the indicator dilution gas and actuating the valving system to return the patient to direct assisted ventilation.

2. The method according to claim 1 which includes supplying supplementary quantities of gasses to the indicator dilution gas.

3. The method according to claim 2 wherein the supplementary gasses are oxygen and nitrogen.

4. Apparatus for obtaining non-invasive cardio-pulmonary measurements comprising, a volume ventilator, a constant volume chamber, a variable volume indicator dilution gas container operatively associated with said chamber, a valving system, means for connecting the valving system to a patient's alveolar environment, and means for sampling and testing for variations in characteristics of an indicator dilution gas from said container, said valving system comprising means for connecting the ventilator to the patient for direct assisted ventilation in one adjusted position and means for connecting the ventilator to the constant volume chamber and for connecting the variable volume container to the patient in another adjusted position to provide for assisted testing, and said sampling and testing means being coupled to said means for connecting the valving system to the patient's alveolar environment.

5. Apparatus according to claim 4 wherein the constant volume chamber is a bottle and the gas container is a flexible gas impermeable bag located within the bottle.

6. Apparatus according to claim 4 which includes means for infusing gas into the gas container.

7. Apparatus according to claim 4 which includes a gas pick-up chamber connected to the sampling and testing means and located between the valving system and the patient.

8. Apparatus according to claim 4 in which said sampling and testing means comprises a mass spectrometer.

* * * * *